United States Patent [19]

Stridde

[11] 3,992,467

[45] Nov. 16, 1976

[54] PROCESS FOR ALKYLATING AROMATIC HYDROCARBONS AND CATALYST THEREFOR

[75] Inventor: George E. Stridde, Houston, Tex.

[73] Assignee: NL Industries, Inc., New York, N.Y.

[22] Filed: Mar. 29, 1976

[21] Appl. No.: 671,507

Related U.S. Application Data

[62] Division of Ser. No. 503,985, Sept. 6, 1974.

[52] U.S. Cl. .................. 260/671 C; 260/671 B; 260/671 P; 260/671 R
[51] Int. Cl.[2] ............................................ C07C 3/52
[58] Field of Search ........ 260/671 C, 671 B, 671 R, 260/671 P

[56] References Cited

UNITED STATES PATENTS

| | | | |
|---|---|---|---|
| 2,853,533 | 9/1958 | Weaver | 260/671 R |
| 2,930,819 | 3/1960 | Aries | 260/671 C |

Primary Examiner—Delbert E. Gantz
Assistant Examiner—C. E. Spresser
Attorney, Agent, or Firm—Roy F. House; Delmar H. Larsen; Robert L. Lehman

[57] ABSTRACT

Alkylatable aromatic hydrocarbons are alkylated with olefins and alkylhalides under anhydrous alkylating conditions in the presence of a metallic cation exchanged trioctahedral 2:1 layer-lattice smectite-type catalyst in which the metallic cation has a Pauling electronegativity greater than 1.0. In a specific embodiment, 1-dodecene is reacted with benzene by contacting the dodecene and benzene under anhydrous conditions in the liquid phase at the boiling point of the mixture with a catalyst comprising a metallic cation such as $Al^{3+}$, $In^{3+}$ and $Cr^{3+}$ exchanged onto the surface of hectorite clay.

21 Claims, No Drawings

PROCESS FOR ALKYLATING AROMATIC HYDROCARBONS AND CATALYST THEREFOR

This is a division of application Ser. No. 503,985, filed Sept. 6, 1974.

This invention relates to a process for the liquid phase alkylation of aromatic hydrocarbons in which the catalyst comprises certain cation-exchanged trioctahedral 2:1 layer lattice smectite-type clays. More particularly, the present invention is concerned with a method wherein an aromatic hydrocarbon, e.g. benzene, and an alkylating agent, e.g. an olefin, are reacted in the liquid phase in the presence of a catalyst which comprises a trioctahedral 2:1 layer-lattice smectite-type mineral which has a metal cation having a Pauling electronegativity greater than 1.0 in ion-exchange positions on the surface of the clay particles.

It has been reported that various materials containing acidic catalytic sites are useful in catalyzing the reaction between aromatic hydrocarbons and various alkylating agents such as olefins and alkyl halides. See for example: the Kirk-Othmer Encyclopedia of Chemical Technology, 2nd Edition, Vol. 1, pp. 882–901 (1963); "Alkylation of Benzene with Dodecene-2 catalyzed by Supported Silicotungstic Acid," R. T. Sebulsky and A. M. Henke, Ind. Eng. Chem. Process Res. Develop., Vol. 10, No. 2, 1971, pp. 272–279; "Organic Molecule and Zeolite Crystal: At the Interface," P. B. Venuto, Chem. Tech., April, 1971, pp. 215–224; "Catalysis by Metal Halides. IV. Relative Efficiencies of Friedel-Crafts Catalysts in Cyclohexane-Methylcyclopentane Isomerization, Alkylation of Benzene and Polymerization of Styrene," G. A. Russell, J. Am. Chem. Soc., Vol. 81, 1959, pp. 4634–4838.

It has also been proposed to use various modified clays as catalysts in various acid catalyzed reactions such as alkylation, isomerization, and the like. See for example the following U.S. Pat. Nos. 3,665,778; 3,665,780; 3,365,347; 2,392,945; 2,555,370; 2,582,956; 2,930,820; 3,360,573; 2,945,072; 3,074,983. The latter patent is the only patent known to me which discloses the use of hectorite clay as a catalyst. Other references which disclose the use of clays as catalysts are as follows: "Acid Activation of Some Bentonite Clays," G. A. Mills, J. Holmes and E. B. Cornelius, J. Phy. & Coll. Chem., Vol. 54, pp. 1170–1185 (1950); "H-Ion Catalysis by Clays," N. T. Coleman and C. McAuliffe, Clays and Clay Minerals, Vol. 4, pp. 282–289 (1955); "Clay Minerals as Catalysts", R. H. S. Robertson, Clay Minerals Bull., Vol. 1, No. 2, pp. 47–54 (1948); "Catalytic Decomposition of Glycerol by Layer Silicates," G. F. Walker, Clay Minerals, Vol. 7, pp. 111–112 (1967); "Styrene Polymerization with Cation-Exchanged Aluminosilicates," T. A. Kusnitsyna and V. M. Brmolko, Vysokomol. Soedin., Ser. B1968, Vol. 10, No. 10, pp. 776–9 — see Chem. Abstracts 70:20373x (1969); "Reactions Catalyzed by Minerals. Part I. Polymerization of Styrene", D. H. Solomon and M. J. Rosser, J. Applied Polymer Science, Vol. 9, 1261–1271 (1965).

I have now found that trioctahedral 2:1 layer-lattice smectite-type minerals, particularly hectorite, which have had their exchangeable cations replaced with a metallic cation having a Pauling electronegativity greater than 1.0 are effective catalysts for the alkylation of an alkylatable aromatic hydrocarbon, e.g. benzene, with an olefin or alkyl halide under anhydrous alkylating conditions in the liquid phase.

Accordingly, it is an object of this invention to provide a process for alkylating in the liquid phase an alkylatable aromatic hydrocarbon with an olefin or alkyl halide under anhydrous alkylating conditions in the presence of a trioctahedral 2:1 layer-lattice smectite-type catalyst which has in its cation exchange positions a metallic cation having a Pauling electronegativity greater than 1.0. It is another object of this invention to provide a method of alkylating aromatic hydrocarbons which comprises contacting in the liquid phase an alkylatable aromatic hydrocarbon with an olefin or alkyl halide in a reaction zone which is substantially free of water and in the presence of an effective amount of a catalyst, said catalyst comprising a metallic cation exchanged trioctahedral 2:1 layer-lattice smectite-type mineral wherein the metallic cation has a Pauling electronegativity greater than 1.0. Other objects and advantages of this invention will become apparent to those skilled in the art upon reading the disclosure and the appended claims.

The catalyst of this invention comprises (1) a metallic cation which has a Pauling electronegativity greater than 1.0 exchanged onto the surface of (2) a trioctahedral 2:1 layer-lattice smectite-type mineral.

Representative metallic cations which are useful in this invention may be derived from the following metals, the Pauling electronegativity of which is given in parentheses (See "The Nature of The Chemical Bond", L. Pauling, 1960, 3rd Edition): Be(1.5), Mg (1.2), Al (1.5), Ga(1.6), In (1.7), Cu (1.9), Ag (1.9), La (1.1), Hf (1.3). Cr (1.6), Mo (1.8), Mn (1.5), Fe (1.8), Ru (2.2), Os (2.2), Co (1.8), Rh (2.2), Ir (2.2), Ni (1.8), Pd (2.2), Pt (2.2), and Ce (1.1). Preferred metallic cations are $Al^{3+}$, $In^{3+}$, $Cr^{3+}$, and the rare earth cations, particularly $La^{3+}$ and $Ce^{3+}$. Mixtures of two or more metallic cations having a Pauling electronegativity greater than 1.0 may be present in the catalyst in cation exchange positions on the surface of the trioctahedral 2:1 layer-lattice smectite-type mineral.

Representative trioctahedral 2:1 layer-lattice smectite-type minerals which are useful in this invention are naturally-occurring hectorite, stevensite, and saponite, and their synthetic structural analogs.

The structure of trioctahedral 2:1 layer-lattice smectite minerals is well known. See for example the following publications, incorporated herein by reference: "The Chemistry of Clay Minerals," C. E. Weaver and L. D. Pollard, 77–86 (1973). Elsevier Scientific Publishing Co.; "Clay Mineralogy," R. E. Grim, 77–92, 2nd Edition (1968). McGraw-Hill Book Co.; "Silicate Science. Vol. I. Silicate Structure," W. Eitel, 234–247 (1964). Academic Press: "Rock-Forming Minerals. Vol. 3. Sheet Silicates," W. A. Detr, R. A. Howie, and J. Zussman, 226–245(1962). John Wiley and Sons, Inc.

The smectite-type minerals useful in this invention can be synthesized hydrothermally. In general a gel containing the required molar ratios of silica, alumina, magnesia and fluoride and having a pH at least 8 is hydrothermally treated at a temperature within the range from 100° C – 325° C, preferably 250° C – 300° C, and preferably at the autogeneous water vapor pressure for a period of time sufficient to crystallize the desired smectite, generally 12 – 72 hours depending on the temperature of reaction. In general as the reaction temperature decreases the reaction time increases for well crystallized smectite-type minerals. Many of the smectite-type minerals can be crystallized from melts of the oxides at very high temperatures, generally greater than 950° C.

The following references incorporated herein by reference, describe processes for the hydrothermal synthesis of smectite-type minerals: "A Study of the Synthesis of Hectorite," W. T. Granquist and S. S. Pollack. Clays and Clay Minerals, Proc. Nat'l. Conf. Clays Clay Minerals. 8, 150–169 (1960); "Synthesis of a Nickel-Containing Montmorillonite," B. Siffert and F. Dennefeld. C. R. Acad. Sci., Paris, Ser. D. 1968, 267 (20), 1545–8 (Reference Chemical Abstracts, Vol. 70; 43448q); "Synthesis of Clay Minerals," S. Caillere, S. Henin, and J. Esquevin. Bull. Groups franc-argiles. 9, No. 4, 67–76 (1957) (Reference Chemical Abstracts 55L8190e) U.S. Pat. No. 3,586,478; U.S. Pat. No. 3,666,407; U.S. Pat. No. 3,671,190.

Hectorite-type clays can be represented by the structural formula:

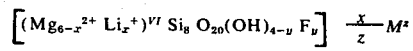

$$\left[(Mg_{6-x}{}^{2+} Li_x{}^+)^{VI} Si_8 O_{20}(OH)_{4-y} F_y\right] \frac{x}{z} - M^z$$

where
$0.33 \leq x \leq 1$
$0 \leq y \leq 4$
and where
M is at least one charge-balancing cation of valence Z. Preferably $0 \leq y \leq 2$ Stevensite-type clays can be represented by the structural formula:

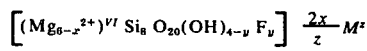

$$\left[(Mg_{6-x}{}^{2+})^{VI} Si_8 O_{20}(OH)_{4-y} F_y\right] \frac{2x}{z} - M^z$$

where
$0.16 \leq x \leq 0.5$
$0 \leq y \leq 4$
and where
M is at least one charge balancing cation of valence Z. Preferably $0 \leq y \leq 2$.

Saponite-type clays can be represented by the structural formula:

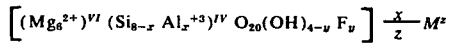

$$\left[(Mg_6{}^{2+})^{VI} (Si_{8-x} Al_x{}^{+3})^{IV} O_{20}(OH)_{4-y} F_y\right] \frac{x}{z} - M^z$$

where
$0.33 \leq x \leq 1$
and where $0 \leq y \leq 4$
M is at least one charge-balancing cation of valence z.
Preferably $0 \leq y \leq 2$.

In the catalyst of the present invention M is at least one metallic cation which has a Pauling electronegativity greater than 1.0. However, before preparing the catalyst by an ion-exchange process, the charge-balancing cation present on the surface of the layer lattices must be a cation capable of being exchanged, preferably $Na^+$, $Li^+$, or $NH_4{}^+$, unless it is a metallic cation which has a Pauling electronegativiy greater than 1.0.

The minerals can contain minor amounts of other metals substituted isomorphously in the layer-lattices for the metals indicated in the above formulas, such as $Fe^{2+}$, and $Al^{3+}$ in the octehedral layer and $Fe^{3+}$ in the tetrahedral layers. Metals having an ionic radius not greater than 0.75 A can be present in the octahedral layer. Metals having an ionic radius not greater than 0.64 A can be present in the tetrahedra layers. Such minor inclusions are common in naturally occurring minerals. Generally the sum of such extraneous isomorphously substituted metals will amount to no more than 5 mole percent based on the metals present in the layer in which the substitution occurs.

The preferred trioctahedral 2:1 layer-lattice smectite-type mineral is hectorite.

The catalyst of the present invention can be prepared by any ion-exchange process wherein a metallic cation having a Pauling electronegativity greater than 1.0 can be made to replace the exchangeable cation of the smectite-type clay. Preferably an aqueous solution of a soluble salt of the desired metallic cation is admixed withe the desired smectite-type clay for a period of time sufficient to effect the desired exchange. Preferably an amount of metallic cation will be used which is from 100 to 500% of the exchange capacity of the smectite-type clay, more preferably 100 to 300%. It is preferred to exchange at least 50 percent of the exchangeable cations of the smectite with the metallic cations of this invention. It is also preferred to remove excess metallic cation salt and the soluble salt by-products of the exchange from the catalyst such as by filtration and washing prior to drying the catalyst. Alternatively the excess metallic cation salt and soluble salt by-product can be removed from the dried catalyst by slurrying the catalyst in an appropriate solvent, such as water or methanol, followed by filtration and re-drying. The exchange can also be conducted using a solution of the metallic cation salt in an appropriate organic solvent, such as methanol. Alternatively, the process disclosed in U.S. Pat. No. 3,725,528 can be used to prepare the catalyst.

The catalyst of this invention has been found to be active in catalyzing the reaction between alkylatable aromatic hydrocarbons and olefin-acting compounds under anhydrous alkylating conditions in the liquid phase.

Alkylatable aromatic hydrocarbons which can be used in the inventive process include benzene, toluene, xylene, the naphthalene series of hydrocarbons, etc. Any aromatic hydrocarbon can be alkylated if it has an unsubstituted carbon as long as steric hindrance does not prevent alkylation with the particular olefin-acting compound chosen for use in the process, and as long as the alkyl side chains on the aromatic ring do not prevent the aromatic compound from being adsorbed onto the layer-lattice surfaces of the catalyst. Benzene is the preferred aromatic hydrocarbon.

The olefin-acting compounds may be selected from the group consisting of mono-olefins, alkyl bromides, alkyl chlorides, and mixtures thereof. Representative olefins include ethylene, propylene, 1-butene, 2-butene, 1-pentene, 2-pentene, 1-hexene, propylene tetramer, 1-octadecene, etc. Representative alkyl halides include n-butyl bromide, r-butyl chloride, n-dodecyl bromide, n-dodecyl chloride, etc.

The process is carried out in the liquid phase utilizing a catalytically effective amount of the catalyst hereinbefore described. The catalyst can be used in amounts from 1 to 100% by weight based on the olefin-acting compound depending on the particular metallic cation-exchanged smeotite-type catalyst chosen for the reaction, the temperature of the reaction, and the length of time the catalyst has been in service. Preferably a concentration of catalyst from 2 to 50% by weight is used since this gives a relatively fast alkylation, still more preferably 2 to 10 percent.

The pressure can be elevated and is not critical as long as some of the olefin-acting compound can be kept dissolved in the liquid aromatic phase. Thus the pressure should be correlated with the temperature at which the reaction is being carried out in order to maintain the aromatic hydrocarbon in the liquid phase and to maintain a sufficient amount of olefin-acting compound dissolved therein to allow the alkylation reaction to proceed. Atmospheric pressure is preferred because of the simplicity of operations under atmospheric conditions.

The process is conducted at an elevated temperature since the rate of alkylation is undesirably low at room temperature. Preferably the temperature is in the range from 40° C to 200° C, more preferably 70° C to 150° C. It is desirable to conduct the process at the boiling point (reflux temperature) of the alkylatable aromatic hydrocarbon provided that it is in the above noted range. A non-alkylatable solvent, such as cyclohexane, can be used to provide the liquid alkylating medium and the temperature can conveniently be maintained at the boiling point of the solvent.

The molar ratio of alkylatable aromatic hydrocarbon to alkylating agent, i.e., the olefin-acting compound, can vary widely depending on the product desired. Thus at higher ratios such as 10 or above essentially only mono-alkylated product is obtained whereas at lower ratios the amount of polyalkylated product is increased. Preferably a molar ratio within the range from 3:1 to 20:1 will be used, more preferably 5:1 to 10:1.

It is important to maintain the reaction system free of water since water has a deactivating effect on the catalyst. Thus the catalyst must be dried before use. This may conveniently be done by removing the water from the catalyst at a low temperature, i.e., less than about 200° C. Alternatively the water may be removed by azeotropic distillation from a mixture of the catalyst in the alkylatable aromatic hydrocarbon or the solvent to be used in the reaction. This method will also remove any water present in these organic systems and is preferred. The term "anhydrous" as used in this specification and in the claims is intended to mean that any free water which is present in the catalyst or the organic components present in the reaction mix is removed from the reaction system.

The following non-limiting examples are given in order to illustrate the invention.

EXAMPLES 1 - 27

Various cation exchanged forms of the natural mineral hectorite were prepared as follows: The exchange cation salt was dissolved in 500 to 750ml. of methanol. Hectorite clay which had been previously dispersed in water, centrifuged, and spray dried in order to obtain the purified clay, was mixed in this salt solution at a concentration of 300 milliequivalents of cation per 100 grams of clay. This mixture was allowed to stand for approximately 20 hours before it was filtered. The filter cake was re-dispersed in 500–750 ml. of methanol followed by filtration for a total of 3 successive washings. The cation exchanged hectorite was then air dried for 20 hours at room temperature followed by oven drying at 105° C for 2 hours. The clay obtained by this process was very fine and needed no grinding. In the case of $Ag^+$-hectorite, 10 ml. of concentrated nitric acid was added to the methanol solution before adding the clay to the solution, in order to prevent oxide formation or hydrolysis of the $Ag^+$.

These cation exchanged hectorite clays were evaluated as catasyts for the alkylation of benzene using the following procedure: 10 grams of the cation exchanged hectorite and 200–250 ml. of benzene are refluxed in a round bottom flask equipped with a Dean-Stark tube attached to remove, azeotropically, sorbed water from the clay. After 2–4 hours the tube was removed and the reflux condenser rinsed with methanol and air dried to remove any residual moisture trapped in the condenser. 10 grams of the alkylating agent were added to the flask and the mixture refluxed with stirring for 24 hours. The clay was removed by filtration and washed with 100 ml. of benzene. The benzene was removed from the filtrate by vacuum evaporation leaving a product of unreacted alkylating agent and/or akylbenzene. This product was then weighed and analyzed by either infrared spectrophotometry, refractometry, or gas chromatography to determine the amount of alkylbenzene formed. The cation exchanged hectorite, evaluated and the data obtained are given in Table 1.

The data indicate that the natural hectorite clay containing exchanged metallic cations having a Pauling electronegativity less than or equal to 1.0 were ineffective as catalysts for the alkylation of benzene. Metallic cations having a Pauling electronegativity greater than 1.0 were effective catalysts when exchanged onto hectorite. These include $Be^{2+}$ and $Mg^{2+}$ (Group IIA), $Al^{3+}$ and $In^{3+}$ (Group IIIA), $La^{3+}$ (Group IIIB), $Cr^{3+}$ (Group VIA), $Mn^{2+}$ (Group VIIB), $Fe^{3+}$, $Co^{2+}$, $Ni^{2+}$ and $Pd^{2+}$ (Group VIII), $Cu^{2+}$ and $Ag^+$ (Group IB), and $Ce^{3+}$ (rare earths). The effect of moisture within the reaction zone on the activity of certain of the catalysts can be ascertained by reference to the data for Examples 1, 4 and 6. The small amount of water which remained in the reflux condenser (Examples 1,6) or in the atmosphere (Example 4) was sufficient to decrease the activity of $Al^{3+}$-exchanged hectorite approximately 50 percent, whereas $In^{3+}$-exchanged hectorite was very active in the presence of such small quantities of water.

TABLE 1

Alkylation of Benzene
Alkylating Agent: Catalyst Weight Ratio = 1:1
Benzene: Alkylating Agent Mole Ratio = 10:1
Temperature = 80.1° C (B.P. of Benzene)
Duration of Reaction = 24 Hours
Catalyst = Various Cation Exchanged Forms of Hectorite

| Example | Exchangeable Cation on Hectorite | Pauling Electro- negativity of Cation | Alkylating Agent | % Yield of Alkyl- benzene |
|---|---|---|---|---|
| 1 | $Al^{3+}$ | 1.5 | n-Butyl Bromide | 80 (36)[a] |
| 2 | $In^{3+}$ | 1.7 | n-Butyl Bromide | 86 |
| 3 | $H^+$ | 2.1 | n-Butyl Bromide | 10 |
| 4 | $Al^{3+}$ | 1.5 | n-Butyl Chloride | 18 (40)[b] |
| 5 | $In^{3+}$ | 1.7 | n-Butyl Chloride | 94 |
| 6 | $Al^{3+}$ | 1.5 | Lauryl Bromide | 89 (48)[a] |
| 7 | $In^{3+}$ | 1.7 | Lauryl Bromide | (86)[a] |
| 8 | $Fe^{3+}$ | 1.8 | Lauryl Bromide | (31)[a] |
| 9 | $Al^{3+}$ | 1.5 | 1-Octadecene | 93[c] |
| 10 | $In^{3+}$ | 1.7 | 1-Octadecene | 93[d] |
| 11 | $Al^{3+}$ | 1.5 | 1-Dodecene | 88 |
| 12 | $Fe^{3+}$ | 1.8 | 1-Dodecene | 88 |
| 13 | $Cr^{3+}$ | 1.6 | 1-Dodecene | 100 |
| 14 | $La^{3+}$ | 1.1 | 1-Dodecene | 100 |
| 15 | $Ce^{3+}$ | 1.1 | 1-Dodecene | 99 |
| 16 | $Be^{2+}$ | 1.5 | 1-Dodecene | 96 |
| 17 | $Mg^{2+}$ | 1.2 | 1-Dodecene | 96 |
| 18 | $Mn^{2+}$ | 1.5 | 1-Dodecene | 92 |
| 19 | $Co^{2+}$ | 1.8 | 1-Dodecene | 91 |

TABLE 1-continued

Alkylation of Benzene
Alkylating Agent: Catalyst Weight Ratio = 1:1
Benzene: Alkylating Agent Mole Ratio = 10:1
Temperature = 80.1° C (B.P. of Benzene)
Duration of Reaction = 24 Hours
Catalyst = Various Cation Exchanged Forms of Hectorite

| Example | Exchangeable Cation on Hectorite | Pauling Electro-negativity of Cation | Alkylating Agent | % Yield of Alkyl-benzene |
|---|---|---|---|---|
| 20 | $Ni^{2+}$ | 1.8 | 1-Dodecene | 93 |
| 21 | $Cu^{2+}$ | 1.9 | 1-Dodecene | 99 |
| 22 | $Pd^{2+}$ | 2.2 | 1-Dodecene | 71 |
| 23 | $Ag^+$ | 1.9 | 1-Dodecene | 100 |
| 24 | $Ca^{2+}$ | 1.0 | 1-Dodecene | 52 |
| 25 | $Ba^{2+}$ | 0.9 | 1-Dodecene | 5 |
| 26 | $Li^+$ | 1.0 | 1-Dodecene | 5 |
| 27 | $Na^+$ | 0.9 | 1-Dodecene | Trace[e] |

[a]Methanol Rinse of Reflux Condenser Omitted
[b]Nitrogen Circulated through the Reaction Flask
[c]Small Amount of n-Butyl Bromide Added to Promote the Reaction
[d]Small amount of Lauryl Bromide added to promote the reaction
[e]Clay without Exchange Treatment - Primarily $Na^+$ Form.

EXAMPLES 28–43

Several cation exchanged hectorites were prepared by at least one of the following procedures as indicated in Table 2: Process A - exchange in methanol solution as in Examples 1–27; Process B - exchange in aqueous solution substituting water for methanol in Process A except in the last washing step; Process c-exchange in aqueous solution, no washing. These catalysts were evaluated for the alkylation of benzene by 1-dodecene at a 1-dodecene:catalyst weight ratio of 10:1 using the same process as in Examples 1-27. The percent conversion of the olefin after one hour is given in Table 2. The catalysts used in Examples 33, 34, 37 and 38 were the same catalysts used in Examples 32, 33, 36 and 37 respectively, after rinsing them with benzene.

The data indicate that water is the preferred solvent for the metallic cation salt, i.e., for the exchange solution, and that the catalyst should be washed to remove soluble salts from the catalyst. The cataysт can be re-used after rinsing with benzene to remove adsorbed products from the catalyst.

TABLE 2

Alkylation of Benzene with 1-Dodecene
Benzene: 1-Dodecene Mole Ratio = 10:1
1-Dodecene: Catalyst Weight Ratio: = 10:1
Temperature = 80.1° C (B.P. of Benzene)
Duration of Run = One Hour

| Example | Exchangeable Cation on Hectorite | 1-Dodecene to Cation Ratio | Catalyst Preparation Process | % Conversion of Olefin |
|---|---|---|---|---|
| 28 | $Al^{3+}$ | 1,000/1 | A | 53 |
| 29 | $Al^{3+}$ | 1,000/1 | B | 95 |
| 30 | $Al^{3+}$ | 1,000/1 | C | 1.2 |
| 31 | $Al^{3+}$ | 1,000/1 | C | 4.4 |
| 32 | $Al^{3+}$ | 1,000/1 | B | 97 |
| 33 | $Al^{3+}$ | 1,000/1 | B | 77[a] |
| 34 | $Al^{3+}$ | 1,000/1 | B | 37[b] |
| 35 | $Cr^{3+}$ | 526/1 | A | 90 |
| 36 | $Cr^{3+}$ | 526/1 | B | 99+ |
| 37 | $Cr^{3+}$ | 526/1 | B | 82[c] |
| 38 | $Cr^{3+}$ | 526/1 | B | 58[d] |
| 39 | $In^{3+}$ | 263/1 | A | 3 |
| 40 | $In^{3+}$ | 263/1 | B | 99 |
| 41 | $Mg^{2+}$ | 833/1 | A | 29 |
| 42 | $Fe^{3+}$ | 357/1 | B | 84 |
| 43 | $Ag^+$ | 256/1 | A | 21 |

[a]The catalyst from the previous experiment, after X hours reaction time and Y% conversion of dodecene, was re-used after it was rinsed with benzene, where X = 4 hours and Y = 99.3%.
[b]As [a], except X = 7 hours and Y = 99.1%
[c]As [a], except X = 1 hours and Y = 99+%
[d]As [a], except X = 3 hours and Y = 93.4%

EXAMPLE 44

A sample of synthetic hectorite, commercially available from N L INDUSTRIES, INC. as BAPASYM[R] LIH, was exchanged with $AlCl_3$ using the process of Examples 1 – 27 to the $Al^{3+}$-exchanged form. This sample was used to catalyze the reaction between n-butyl bromide and benzene using the same process and conditions as in Examples 1 – 27. 62% of this alkylating agent were converted to alkylbenzene.

EXAMPLE 45

A sample of synthetic $Na^+$-stevensite was exchanged to the $Al^{3+}$ form with $AlCl_3$ using the aqueous exchange process B of Examples 28 – 43. This $Al^{3+}$-stevensite was characterized by the structural formula:

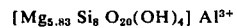

$$[Mg_{5.83} Si_8 O_{20}(OH)_4] Al^{3+}$$

This sample was evaluated as a catalyst for the conversion of 1-dodecene and benzene to dodecylbenzene as in Examples 28–43. 44% of the dodecene was converted to dodecylbenzene after one hour.

EXAMPLES 46 – 47

$Al^{3+}$-exchanged hectorite was used to catalyze the alkylation of anthracene with 1-octadecene by refluxing anthracene and 1-octadecene in a molar ratio of 10:1 and an octadecene:catalyst ratio of 1:1 in cyclohexane. No octadecene was detectable after 24 hours. Similar results were obtained when biphenyl was substituted for the anthracene.

EXAMPLE 48

A sample of synthetic $Na^+$-saponite containing occluded MgO was exchanged with $AlCl_3$ using the process of Example 44. The $Al^{3+}$-saponite is characterized by the structural formula:

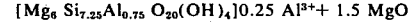

$$[Mg_6 Si_{7.25}Al_{0.75} O_{20}(OH)_4]0.25 Al^{3+} + 1.5 MgO$$

This sample was evaluated as in Examples 28–43. 74% of the dodecene was converted to dodecylbenzene after one hour.

EXAMPLES 49 – 59

An $Al^{3+}$-exchanged hectorite and a $Cr^{3+}$-exchanged hectorite (purified natural clay as in Example 1–27) were prepared by the aqueous exchange process B of Examples 28–43. These clays were evaluated as catalysts for the alkylation of benzene by 1-dodecene at various mole ratios of benzene to dodecene and/or various weight ratios of dodecene to cataysт as indicated in Table 3. The percent conversion of dodecene after 1 hour and, in some cases, 24 hours using the same process as in Examples 1 – 27 was determined. The data obtained are given in Table 3.

The data indicate that these exchanged clays were excellent catalysts at concentrations of exchanged clay greater than about 2 percent, based on the weight of dodecene, although concentrations as low as 1 percent converted most of the dodecene in 24 hours.

TABLE 3

Alkylation of Benzene with 1-Dodecene
Benzene: 1-dodecene Mole Ratio: as indicated
1-dodecene:Catalyst Weight Ratio: as indicated
Temperature: 80.1° C (B.P. of Benzene)
Duration of Run: 1, 24 Hours
Catalyst: Al$^{3+}$- and Cr$^{3+}$-exchanged Hectorite as indicated

| Ex. | Exchangeable Cation on Hectorite | 1-dodecene to Catalyst Wt. Ratio | Benzene to 1-dodecene Mole Ratio | % Conversion of 1-dodecene 1 Hr. | 24 Hr. |
|---|---|---|---|---|---|
| 49 | Cr$^{3+}$ | 10:1 | 10:1 | 99.6 | — |
| 50 | Cr$^{3+}$ | 20:1 | 10:1 | 98.4 | — |
| 51 | Cr$^{3+}$ | 40:1 | 10:1 | 70.1 | — |
| 52 | Cr$^{3+}$ | 100:1 | 10:1 | 43.7 | 83.8 |
| 53 | Al$^{3+}$ | 10:1 | 10:1 | 97.0 | — |
| 54 | Al$^{3+}$ | 20:1 | 10:1 | 98.2 | — |
| 55 | Al$^{3+}$ | 40:1 | 10:1 | 82.1 | 99.0 |
| 56 | Al$^{3+}$ | 50:1 | 5:1 | 55.2 | 90.2 |
| 57 | Al$^{3+}$ | 100:1 | 10:1 | 34.2 | 78.0 |
| 58 | Al$^{3+}$ | 100:1 | 5:1 | 18.9 | 71.6 |
| 59 | Al$^{3+}$ | 100:1 | 20:1 | 29.6 | 67.1 |

EXAMPLE 60

A sample of synthetic hectorite-type clay commercially available as LAPONITE B was exchanged with AlCl$_3$ using process B of Examples 28 – 43 to the Al$^{3+}$-exchanged form. This sample was used to catalyze the reaction between 1-dodecene and benzene as in Examples 28 – 43. 88% of the dodecene was converted to dodecylbenzene after 1 hour.

As indicated, the trioctahedral 2:1 layer-lattice smetite-type clay minerals useful in preparing the catalysts for the catalytic processes described and hereinafter claimed can be prepared synthetically by either a hydrothermal process or a pneumatolytic process. Such smectite-type clays can be synthesized having one or more metallic cations having an ionic radius not greater than 0.75 A in the central octahedral layer and having one or more metallic cations having an ionic radius not greater than 0.64 A in the two outer tetrahedral layers. Thus such synthetic trioctahedral 2:1 layer-lattice smectite-type clays have the following general structural formula:

$$\left[(aM^{+1} + bM^{+2} + cM^{+3})^{VI} (dD^{+3} + eD^{+4} + fD^{+5})^{IV} O_{20}(OH)_{4-y}F_y\right] \frac{x}{z} R^z$$

ps where
where

| | |
|---|---|
| 11 ≤ a+2b+3c ≤ 12 | 0 ≤ a ≤ 1 |
| 31 ≤ 3d+4e+5f ≤ 32 | 5 ≤ b ≤ 6 |
| 43 ≤ a+2b+3c+3d+4e+5f ≤ 43.67 | 0 ≤ c ≤ 0.3 |
| x = 44−(a+2b+3c+3d+4e+5f) | 0 ≤ d ≤ 1 |
| 0 ≤ y ≤ 4 | 7 ≤ e ≤ 8 |
| | 0 ≤ f ≤ 0.4 | and where the metallic cations M are in the octahedral layer and have an ionic radius not greater than 0.75 A, the metallic cations D are in the two outer tetrahedral layers and have an ionic radius not greater than 0.64 A, and R is at least one exchangeable charge-balancing cation of valence z.

Preferably the cation M is selected from the group consisting of Li$^+$, Mg$^{2+}$, Ni$^{2+}$, Co$^{2+}$, Zn$^{2+}$, Cu$^{2+}$, Mn$^{2+}$, Al$^{3+}$, and mixtures thereof, the cation D is selected from the group consisting of Al$^{3+}$, Cr$^{3+}$, Fe$^{3+}$, Si$^{+4}$, Ge$^{+4}$, and mixtures thereof, and the cation R is selected from the group consisting of Li$^+$, Na$^+$, NH$_4^+$, and mixture thereof.

Such synthetic hectorite-type clays can be represented by th structural formula: the $$\left[(M_{6-x}^{2+} Li_x^+)^{VI} (D_8^{+4}) O_{20}(OH)_{4-y} F_y\right] \frac{x}{z} R^z$$

where $0.33 \leq x \leq 1$ and $0 \leq y \leq 4$.

Such synthetic saponite-type clays can be represented by the structural formula:

$$\left[(M_6^{+2})^{VI} (D_{8-x}^{+4} D_x^{+3})^{IV} O_{20}(OH)_{4-y}F_y\right] \frac{x}{z} R^z$$

where $0.33 \leq x \leq 1$ and $0 \leq y \leq 4$.

It will be understood that while I have explained the invention with the aid of specific examples, nevertheless considerable variation is possible in choice of raw materials, proportions, processing conditions and the like, within the broad scope of the invention as set forth in the claims which follow. Thus, for example, my inventive catalyst may be used simultaneously with other catalytic materials so as to suit particular conditions and circumstances.

I claim:

1. In a process for alkylating in the liquid phase an alkylatable aromatic hydrocarbon with an olefin-acting compound selected from the group consisting of monoolefins, alkyl bromides, alkyl chlorides, and mixtures thereof, the improvement which comprises contacting said hydrocarbon and said compound under anhydrous alkylating conditions with a catalyst comprising a trioctahedral 2:1 layer-lattice smectite-type mineral containing a metallic cation having Pauling electronegativity greater than 1.0 in cation exchange positions on the surface of said mineral.

2. The process of claim 1 wherein said catalyst is selected from the group consisting of:
   a. hectorite-type clays having the following structural formula:

$$\left[(Mg_{6-x}^{2+} Li_x^+)^{VI} Si_8 O_{20}(OH)_{4-y} F_y\right] \frac{x}{z} M^z$$

where
   $0.33 \leq x \leq 1$
   $0 \leq y \leq 4$
   and
   M is at least one metallic cation having a Pauling electronegativity greater than 1.0 of valence z;
   b. stevensite-type clays having the following structural formula:

$$\left[(Mg_{6-x})^{VI} Si_8 O_{20}(OH)_{4-y}F_y\right] \frac{2x}{z} M^z$$

where
 0.16 ≤ x ≤ 0.5
 0 ≤ y ≤ 4
and
M is at least one metallic cation having a Pauling electronegativity greater than 1.0 of valence z; and
c. saponite-type clays having the following structural formula:

$$\left[(Mg_6{}^{2+})^{VI}(Si_{8-x}Al_x{}^{3+})^{IV}O_{20}(OH)_{4-y}F_y\right]\frac{-x}{z}M^z$$

where
 0.33 ≤ x ≤ 1
 0 ≤ y ≤ 4
and
M is at least one metallic cation having a Pauling electronegativity greater than 1.0 of valence z.

3. The process of claim 2 wherein 0 ≤ y ≤ 2 in all of said clays.

4. The process of claim 3 wherein said aromatic hydrocarbon is benzene and wherein said olefin-acting compound is a mono-olefin.

5. The process of claim 4 wherein said mono-olefin is dodecene.

6. The process of claim 3 wherein said cation is selected from the group consisting of $Al^{3+}$, $Cr^{3+}$, $Ga^{3+}$, $In^{3+}$, $Mn^{2+}$, $Fe^{3+}$, $Co^{3+}$, $Co^{2+}$, $Ni^{2+}$, $Cu^{2+}$, $Ag^+$, $Be^{2+}$, $Mg^{2+}$, $La^{3+}$, $Ce^{3+}$, $Pd^{2+}$, and mixtures thereof.

7. The process of claim 3 wherein said cation is selected from the group consisting of $Al^{3+}$, $Cr^{3+}$, $In^{3+}$, the rare earths and mixtures thereof.

8. The process of claim 7 wherein said hydrocarbon is benzene and said compound is a mono-olefin.

9. The process of claim 7 wherein said mineral is said hectorite-type clay.

10. The process of claim 9 wherein said hydrocarbon is benzene and wherein said compound is a mono-olefin.

11. A process for alkylating aromatic hydrocarbons which comprises contacting in the liquid phase an alkylatable aromatic hydrocarbon with an olefin-acting compound selected from the group consisting of mono-olefins, alkyl bromides, alkyl chlorides, and mixtures thereof, under alkylating conditions in a reaction zone which is substantially free of water and in the presence of an effective amount of a catalyst, said catalyst comprising a metallic cation exchanged trioctahedral 2:1 layer-lattice smectite-type mineral wherein said metallic cation has a Pauling electronegativity greater than 1.0.

12. The process of claim 11 wherein said mineral is selected from the group consisting of hectorite, stevensite, and saponite.

13. The process of claim 12 wherein said cation is selected from the group consisting of $Al^{3+}$, $Cr^{3+}$, $In^{3+}$, the rare earths, and mixtures thereof.

14. The process of claim 13 wherein said hydrocarbon is benzene and wherein said compound is a mono-olefin.

15. The process of claim 14 wherein said mono-olefin is dodecene.

16. A process for alkylating benzene with a mono-olefin which comprises contacting in the liquid phase said benzene and said olefin in a reaction zone under anhydrous alkylating conditions in the presence of an effective amount of a catalyst, said catalyst comprising a metallic cation-exchanged trioctahedral 2:1 layer-lattice smectite-type mineral wherein said metallic cation has a Pauling electronegativity greater than 1.0.

17. The process of claim 16 wherein the pressure is atmospheric, the temperature is the boiling point of benzene, the molar ratio of benzene to olefin is from about 5:1 to 10:1, and the weight ratio of olefin to said catalyst is from about 2:1 to 20:1.

18. The process of claim 17 wherein said mineral is selected from the group consisting of hectorite, stevensite, and saponite.

19. The process of claim 18 wherein said cation is selected from the group consisting of $Al^{3+}$, $Cr^{3+}$, $In^{3+}$, the rare earths, and mixtures thereof.

20. The process of claim 19 wherein said olefin is dodecene.

21. The process of claim 20 wherein water is removed from said catalyst by azeotropic distillation from a catalyst-benzene mixture before addition of said dodecene.

* * * * *